United States Patent [19]

Koeffer et al.

[11] Patent Number: 5,081,313
[45] Date of Patent: Jan. 14, 1992

[54] PROCESS FOR THE PREPARATION OF 2,3-DIALKOXYPROPANALS

[75] Inventors: Dieter Koeffer, Weinheim; Robert Maerkl, Fussgoenheim; Werner Bertleff, Viernheim, all of Fed. Rep. of Germany

[73] Assignee: BASF Aktiengesellschaft, Ludwigshafen, Fed. Rep. of Germany

[21] Appl. No.: 528,021

[22] Filed: May 23, 1990

[30] Foreign Application Priority Data

Jun. 22, 1989 [DE] Fed. Rep. of Germany ....... 3920423

[51] Int. Cl.⁵ ..................... C07C 45/50; C07C 47/198
[52] U.S. Cl. ................................... 568/454; 568/448; 568/489; 568/496; 568/497
[58] Field of Search ............... 568/451, 454, 489, 448, 568/496

[56] References Cited

U.S. PATENT DOCUMENTS

| | | | |
|---|---|---|---|
| 2,479,068 | 4/1949 | Gresham | 568/596 |
| 2,880,241 | 3/1959 | Hughes | 568/454 |
| 3,527,809 | 9/1970 | Pruett et al. | 568/454 |
| 3,888,880 | 6/1975 | Snapp, Jr. et al. | 568/454 |
| 3,917,661 | 11/1975 | Pruett et al. | |
| 4,871,878 | 10/1989 | Puckette et al. | 568/454 |

FOREIGN PATENT DOCUMENTS 3403427  8/1985  Fed. Rep. of Germany ...... 568/454

OTHER PUBLICATIONS

J. Biol. Chem. vol. 145 (1942) 61.
Federonko et al., Carbohyd. Res. 87 (1989) 51.
Chem. Zvesti 36 (1982) 837.
J. Mol. Cat. 40 (1987) 129–182.
Baganz et al., Chem. Ber. vol. 96 (1963) 2657–2660.

Primary Examiner—Werren B. Lone
Attorney, Agent, or Firm—John H. Shurtleff

[57] ABSTRACT

The preparation of 2,3-dialkoxypropanals of the general formula I

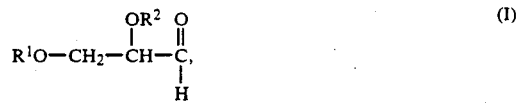

in which $R^1$ and $R^2$ denote $C_1$-$C_8$-alkyl or $C_5$- or $C_6$-cycloalkyl which may or may not bear substituents which are inert under the conditions of the reaction, wherein a 1,2-dialkoxy ethene of the general formula II $$R^1O-HC=CH-OR^2 \qquad (II)$$

is reacted with carbon monoxide and hydrogen in the presence of a rhodium-containing catalyst.

11 Claims, No Drawings

PROCESS FOR THE PREPARATION OF 2,3-DIALKOXYPROPANALS

The present invention relates to a process for the preparation of 2,3-dialkoxypropanals of the general formula I

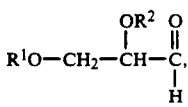

$$R^1O-CH_2-\underset{H}{\underset{|}{CH}}-\overset{O}{\overset{\|}{C}},\quad \text{(with } OR^2 \text{ on the CH)} \tag{I}$$

in which $R^1$ and $R^2$ denote $C_1$-$C_8$-alkyl or $C_5$- or $C_6$-cycloalkyl which may or may not bear substituents which are inert under the conditions of the reaction.

Hitherto, 2,3-dialkoxypropanals have only been obtainable from carbohydrate derivatives. For example, the simplest member of this class of compounds, 2,3-dimethoxypropanal, could only be prepared, hitherto, by oxidizing 1,2,5,6-tetra-O-methylmannitol with lead (IV) acetate [*Baer et al., J. Biol. Chem.* 145, 61 (1942)] or with sodium periodate [*Federonko et al., Carbohyd. Res.* 87, 51 (1989)] or, alternatively, by etherifying glyceraldehyde dimethylacetal with methyl iodide/sodium hydride followed by acetal hydrolysis [*Chem. Zvesti* 36, 837 (1982)]. However, these processes are only suitable for laboratory-scale work, since the preparation of the starting substances alone demands multi-stage syntheses.

Although the preparation of aldehydes via hydroformylation is an industrial process which is utilized in a variety of ways, nothing has as yet been disclosed on the hydroformylation of 1,2-dialkoxy ethenes [*cf. Botteghi et al., J. Mol. Cat.* 40, 129–182 (1987), especially p. 147, chapter 3.2.]. On the other hand, the hydroformylation of vinyl ethers has been described by Lin et al. (U.S. Pat. No. 4,533,756). Snapp et al. (U.S. Pat. No. 3,888,880) merely describe the highly specialized synthesis of dioxane carbaldehyde by the hydroformylation of dioxene using cobalt naphthenate as catalyst.

Since 2,3-dialkoxypropanals are intermediates suitable for a variety of uses and since, in addition, the base-catalyzed elimination of alcohol therefrom gives 2-alkoxyacroleins which are themselves widely useful as monomers and intermediates, it is an object of the invention to provide a process making it possible to manufacture 2,3-dialkoxypropanals on an industrial scale and in a simple and economic manner.

Accordingly, we have found a process for the preparation of 2,3-dialkoxypropanals of the general formula I

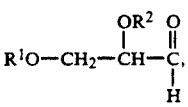

$$R^1O-CH_2-\underset{H}{\underset{|}{CH}}-\overset{O}{\overset{\|}{C}},\quad \text{(with } OR^2 \text{ on the CH)} \tag{I}$$

in which $R^1$ and $R^2$ denote $C_1$-$C_8$-alkyl or $C_5$- or $C_6$-cycloalkyl which may or may not bear substituents which are inert under the conditions of the reaction, which is characterized in that a 1,2-dialkoxy ethene of the general formula II

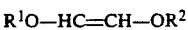

$$R^1O-HC=CH-OR^2 \tag{II}$$

is reacted with carbon monoxide and hydrogen in the presence of a rhodium-containing catalyst.

$R^1$ and $R^2$ may be the same or different and denote $C_1$-$C_6$-alkyl and/or $C_5$-$C_6$-cycloalkyl. The groups $R^1$ and $R^2$ may optionally bear 1 and 2 substituents inert under the conditions of the reaction, for example alkoxy, acetal or ester groups. Preferably, however, $R^1$ and $R^2$ stand for unsubstituted $C_1$-$C_8$-alkyl groups or $C_5$- or $C_6$-cycloalkyl groups, $C_1$-$C_4$-alkyl groups being the preferred alkyl groups. More specifically, $R^1$ and $R^2$ denote, for example, methyl, ethyl, propyl, isopropyl, butyl, isobutyl, t-butyl, pentyl, hexyl, heptyl, octyl, 2-ethylhexyl, cyclopentyl or cyclohexyl.

The starting material used for the preparation of the 2,3-dialkoxypropanals I are dialkoxy ethenes II substituted by appropriate groups $R^1$ and $R^2$ and obtainable in a simple manner by magnesium-catalyzed elimination of chlorine from 1,2-dialkoxy-1,2-dichloroethanes [*cf. Baganz et al. Chem. Ber.* 96, 2657 (1963)] or by the elimination of alcohol from 1,1,2-trialkoxy ethanes in the gas phase using barium hydroxide/silica gel (U.S. Pat. No. 2,479,068) or zeolite (EP-A 302,486) as catalyst.

To prepare the 2,3-dialkoxypropanals I, the dialkoxy ethenes II are reacted with a gaseous mixture comprising carbon monoxide and hydrogen in the presence of a rhodium-containing catalyst. Suitable rhodium-containing catalysts are rhodium compounds such as are described in U.S. Pat. No. 2,880,241, particularly rhodium salts such as rhodium acetate or rhodium acetonylacetonate, rhodium oxides and rhodium carbonyl compounds. We particularly prefer to prepare the 2,3-dialkoxypropanals using a catalyst system consisting of rhodium and a tertiary phosphorus compound. Catalysts of this kind which are suitable for carrying out hydroformylations are known in the art. For example, the catalyst systems described in DE-A 1,793,069 and comprising rhodium and tertiary phosphorus compounds may be used in the process of the invention. Those catalyst systems are preferred in which the tertiary phosphorus compound is a triaryl phosphine or triaryl phosphite, for example triphenyl phosphine, tritolyl phosphine, triphenyl phosphite and tritolyl phosphite.

The catalyst system consisting of rhodium and tertiary phosphorus compound may be a rhodium complex such as is described in DE-A 1,793,069. However, it may be advantageously prepared in situ, i.e. in the reaction mixture subjected to hydroformylation in the presence of hydrogen and carbon monoxide, from a rhodium source and a tertiary phosphorus compound. A suitable rhodium source is, for example, a rhodium salt, a rhodium carbonyl compound or a rhodium oxide. The tertiary phosphorus compound will generally be used in excess of the rhodium, the molar ratio being from 2:1 to 300:1 and preferably from 3:1 to 200:1.

The hydroformylation of the dialkoxy ethenes II may be carried out in the presence of solvents inert under the conditions of the reaction. Suitable solvents are ethers such as diphenyl ether or dioxane, acetals such as 1,3-dioxane, esters such as dibutyl phthalate, and aliphatic or aromatic hydrocarbons such as hexane, cyclohexane and toluene.

The reaction is generally carried out by placing the dialkoxy ethene II in an autoclave together with the components for creating the rhodium catalyst and, possibly, solvent and subjecting this mixture to a carbon monoxide/hydrogen pressure generally of from 2 to 300 bar and preferably from 5 to 100 bar, at a temperature of from 50° to 200° C. and preferably from 60° to 180° C.

and more preferably from 80° to 150° C. The molar ratio of carbon monoxide to hydrogen may vary over a wide range. Conveniently, however, the carbon monoxide:hydrogen ratio is from 0.1:1 to 2:1 molar. It is particularly preferred to use a carbon monoxide/hydrogen gas mixture such as occurs in the manufacture of synthesis gas.

The reaction may be carried out batchwise or continuously in a tubular reactor. The 2,3-dialkoxypropanals obtained may be isolated from the discharged reaction mixture by distillation.

EXAMPLES

EXAMPLE 1

An autoclave having a capacity of 300 ml was filled with 0.56 mole of 1,2-dimethoxy ethane, 40 g of cyclohexane, 0.2 mmole of hydridocarbonyltris(triphenylphosphine) rhodium and 20 mmoles of triphenyl phosphine. At room temperature, a pressure of 20 bar was set up by pumping in a gaseous mixture of carbon monoxide and hydrogen (molar ratio $CO:H_2 = 1:1$).

The reaction mixture was heated to 130° C. in the autoclave, in which the pressure was increased to 70 bar by pumping in more $CO/H_2$-mixture. Following a reaction time of 3 hours, the autoclave was cooled and depressurized. 2,3-Dimethoxypropanal was isolated from the liquid reaction mixture by fractional distillation. Yield = 61%.

EXAMPLE 2

An autoclave having a capacity of 300 ml was filled with 1:1 moles of 1,2-dimethoxy ethene and 0.08 mmole of (acetylacetonato)dicarbonyl rhodium. A pressure of 20 bar was set up by pumping in a carbon monoxide/hydrogen gas mixture as in Example 1.

The reaction mixture was heated to a temperature of 100° C. and the pressure in the autoclave was raised to 280 bar by pumping in more carbon monoxide/hydrogen gas mixture. These conditions were maintained for a reaction time of 8 hours. 2,3-Dimethoxypropanal was present in the discharged reaction mixture (127.8 g) of the extent of 82.5% w/w, as determined by GC analysis.

We claim:

1. A process for the preparation of a 2,3-dialkoxy-propanal of the formula

in which $R^1$ and $R^2$ denote $C_1$-$C_8$-alkyl or $C_5$- or $C_6$-cycloalkyl which optionally bear substituents which are inert under the conditions of the reaction, which process comprises:

reacting a 1,2-dialkoxy ethene of the formula

in which $R^1$ and $R^2$ have the same meaning given above, with carbon monoxide and hydrogen in the presence of a rhodium-containing catalyst at a pressure of from 2 to 300 bar and at a temperature of from 50° to 200° C.

2. A process a claimed in claim 1, wherein the reaction is carried out in the presence of a catalyst system comprising rhodium and a tertiary phosphorus compound.

3. A process as claimed in claim 2, wherein the molar ratio of the tertiary phosphorus compound to rhodium is from 3:1 to 200:1.

4. A process as claimed in claim 2, wherein the tertiary phosphorus compound used is a triaryl phosphine or triaryl phosphite.

5. A process as claimed in claim 1, wherein the molar ratio of carbon monoxide to hydrogen is about 0.1:1 to 2:1.

6. A process as claimed in claim 1, wherein the pressure is from 5 to 100 bar and the temperature is from 60° to 180° C.

7. A process as claimed in claim 6, wherein the temperature is from 80° to 150° C.

8. A process as claimed in claim 2, wherein the pressure is from 5 to 100 bar and the temperature is from 60° to 180° C.

9. A process as claimed in claim 8, wherein the temperature is from 80° to 150° C.

10. A process as claimed in claim 1, wherein the reaction is carried out with a rhodium-containing catalyst but in the absence of a tertiary phosphorus compound.

11. A process as claimed in claim 10, where the reaction is carried out in the absence of a solvent.

* * * * *

UNITED STATES PATENT AND TRADEMARK OFFICE
CERTIFICATE OF CORRECTION

PATENT NO. : 5,081,313
DATED : January 14, 1992
INVENTOR(S) : Koeffer et al.

It is certified that error appears in the above-identified patent and that said Letters Patent is hereby corrected as shown below:

Col. 3, (Claim 1) lines 56 and 47, and col. 4, lines 2-18, should read as follows:

--1. A process for the preparation of a 2,3-dialkoxypropanal of the formula

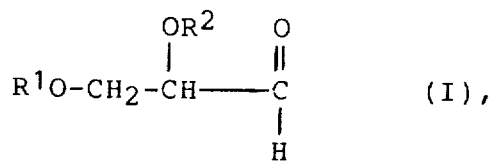

in which $R^1$ and $R^2$ [denote] are selected from the group consisting of unsubstituted $C_1$-$C_8$-alkyl, [or $C_5$- or] unsubstituted $C_5$-$C_6$-cycloalkyl [which optionally bear] and said alkyl and cycloalkyl bearing substituents which are inert under the conditions of the reaction, which process comprises:
reacting a 1,2-dialkoxy ethene of the formula

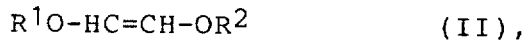

in which $R^1$ and $R^2$ have the same meaning given above, with carbon monoxide and hydrogen in the presence of a rhodium-containing catalyst at a pressure of from 2 to 300 bar

UNITED STATES PATENT AND TRADEMARK OFFICE
CERTIFICATE OF CORRECTION

PATENT NO. : 5,081,313

DATED : January 14, 1992

INVENTOR(S) : Koeffer, et. al.

It is certified that error appears in the above-identified patent and that said Letters Patent is hereby corrected as shown below:

and at a temperature of from 50 to 200°C. --

Signed and Sealed this

Twenty-fifth Day of May, 1993

Attest:

MICHAEL K. KIRK

Attesting Officer

Acting Commissioner of Patents and Trademarks